United States Patent

Champion

[11] Patent Number: 5,898,308
[45] Date of Patent: Apr. 27, 1999

[54] TIME-BASED METHOD AND DEVICE FOR DETERMINING THE DIELECTRIC CONSTANT OF A FLUID

[75] Inventor: James R. Champion, Sarasota, Fla.

[73] Assignee: Teleflex Incorporated, Plymouth Meeting, Pa.

[21] Appl. No.: 08/938,988

[22] Filed: Sep. 26, 1997

[51] Int. Cl.⁶ .......................... G01R 27/04; G01N 22/00; G01F 23/00
[52] U.S. Cl. .......................... 324/643; 324/642; 73/304 R
[58] Field of Search ..................... 324/633, 634, 324/637, 642, 643, 71.1; 73/290 K, 304 R, 304 C

[56] References Cited

U.S. PATENT DOCUMENTS

| | | | |
|---|---|---|---|
| 3,626,284 | 12/1971 | Bak ........................................... | 324/642 |
| 3,789,296 | 1/1974 | Caruso, Jr. et al. ..................... | 324/643 |
| 3,812,422 | 5/1974 | De Carolis ............................... | 324/642 |
| 3,832,900 | 9/1974 | Ross ....................................... | 73/290 R |
| 3,995,212 | 11/1976 | Ross ......................................... | 324/642 |
| 4,489,601 | 12/1984 | Rao et al. ............................. | 73/290 R |
| 4,495,807 | 1/1985 | Field et al. ............................. | 73/290 R |
| 5,376,888 | 12/1994 | Hook ....................................... | 324/643 |
| 5,457,990 | 10/1995 | Oswald et al. ........................ | 73/290 V |
| 5,459,403 | 10/1995 | Kohler et al. ........................... | 324/643 |
| 5,656,774 | 8/1997 | Nelson et al. .......................... | 73/290 V |

*Primary Examiner*—Diep N. Do
*Attorney, Agent, or Firm*—Howard & Howard

[57] ABSTRACT

A device utilizes micropower, impulse radar and time domain reflectometry to determine the dielectric constant of a fluid. An electrically conductive probe preferably in the form of a transmission line, is inserted at least partially into the fluid. The device includes a signal generator that generates an impulse signal that is propagated along the probe. The time that it takes for the signal to reach the end of the probe is determined. The time of travel of the signal along the probe is then used to determine the dielectric constant of the fluid.

20 Claims, 3 Drawing Sheets

TIME-BASED METHOD AND DEVICE FOR DETERMINING THE DIELECTRIC CONSTANT OF A FLUID

BACKGROUND OF THE INVENTION

This invention generally relates to a method and device for determining the dielectric constant of a fluid using the time it takes a signal to travel along a probe that is inserted at least partially into the fluid.

There are a variety of situations where determining the dielectric constant of a fluid is necessary or would be useful. For example, diesel engines can develop cracks or leaks in cylinder liners, head gaskets and other components because of the heavy-duty work performed using diesel powered vehicles. Any one of these problems may present the potential for water to contaminate the oil in the engine. It is important to quickly detect the presence of water within oil because that presents potential engine failure or damage problems. Therefore, it would be useful to determine the dielectric constant of the oil on a routine basis so that the presence of water could be easily determined. Other uses for determining dielectric constants include determining mixtures of fuels and other liquids where the exact content of the liquid may vary. Another example would be to determine the quality of engine oil to facilitate changing the oil at an optimal time.

A number of proposals have been made for determining the dielectric constant of a fluid. For example, U.S. Pat. No. 3,812,422 describes a method that measures a dielectric constant based upon an amplitude of a reflected signal that reflects from an interface between different media such as air and fluid. The amplitude of the reflected signal provides impedance information that then is utilized to calculate the dielectric constant.

Although such a solution may be workable, it is not without shortcomings and drawbacks. A system that utilizes the amplitude of such a reflected signal requires using a variety of components including a peak detector with reset circuitry, a precision reference, and an analog-to-digital converter. Obviously, incorporating these various components can become cumbersome and overly expensive for some applications. Moreover, a system that relies on the amplitude of such a reflected signal is not as accurate as required for many applications because the measurements and the associated components needed to take those measurements are sensitive to temperature and other drift phenomena. In the diesel engine example described above temperatures can become very high. A further problem becomes evident in trying to compensate for signal drift in such systems.

This invention addresses the need for providing a method and device suitable for measuring a dielectric constant of a fluid in a variety of applications. This invention is especially useful and advantageous in situations where the level of a liquid also is determined.

SUMMARY OF THE INVENTION

In general terms, this invention is a device for determining the dielectric constant of a fluid. An electrically conductive probe is placed at least partially into the fluid. A generator that generates an electrical signal is coupled to the probe so that the electrical signal is propagated along the probe from one end toward the other end, which is immersed in the fluid. A signal receiver that is coupled to the probe receives a reflection signal that is a reflection of the propagated signal from the end of the probe that is immersed in the fluid. Determining means determine a time that it takes the propagated signal to travel between the two ends of the probe based upon the reflection signal. The determining means determines the permittivity of the fluid using the time that it takes the signal to travel to the end of the probe.

The method of this invention includes several basic steps. First, a probe is inserted at least partially into the fluid where the dielectric constant is to be determined. A signal is generated and then propagated along the probe. A travel time is then determined between the beginning of the signal moving along the probe and a reflection time when the signal reflects from the end of the probe that is inserted into the fluid. The permittivity of the fluid is then determined based upon the travel time.

In the preferred embodiment, the device of this invention is used to determine a level of the fluid that is under investigation. A signal propagated along the probe reflects back toward the signal receiver when the signal encounters the interface between air and the fluid. There is a reflection because the impedance of the fluid is different than the impedance of the air. The signal continues down the length of the probe to the end of the probe immersed in the fluid. A second reflection occurs at the end of the probe because the end of the probe represents a very high impedance. The time when the reflection at the air/fluid interface occurs and the time when the reflection from the end of the probe occurs are both determined. Those two times and a calibration factor are used to determine the dielectric constant of the fluid. The calibration factor preferably is equal to a total travel time that the signal would travel along the entire length of the probe when the probe is completely immersed in a fluid having a known dielectric constant such as air.

The various features and advantages of this invention will become apparent to those skilled in the art from the following detailed description of the presently preferred embodiment. The drawings that accompany the detailed description can be briefly described as follows.

DETAILED DESCRIPTION OF THE PREFERRED EMBODIMENT

Figure 1:
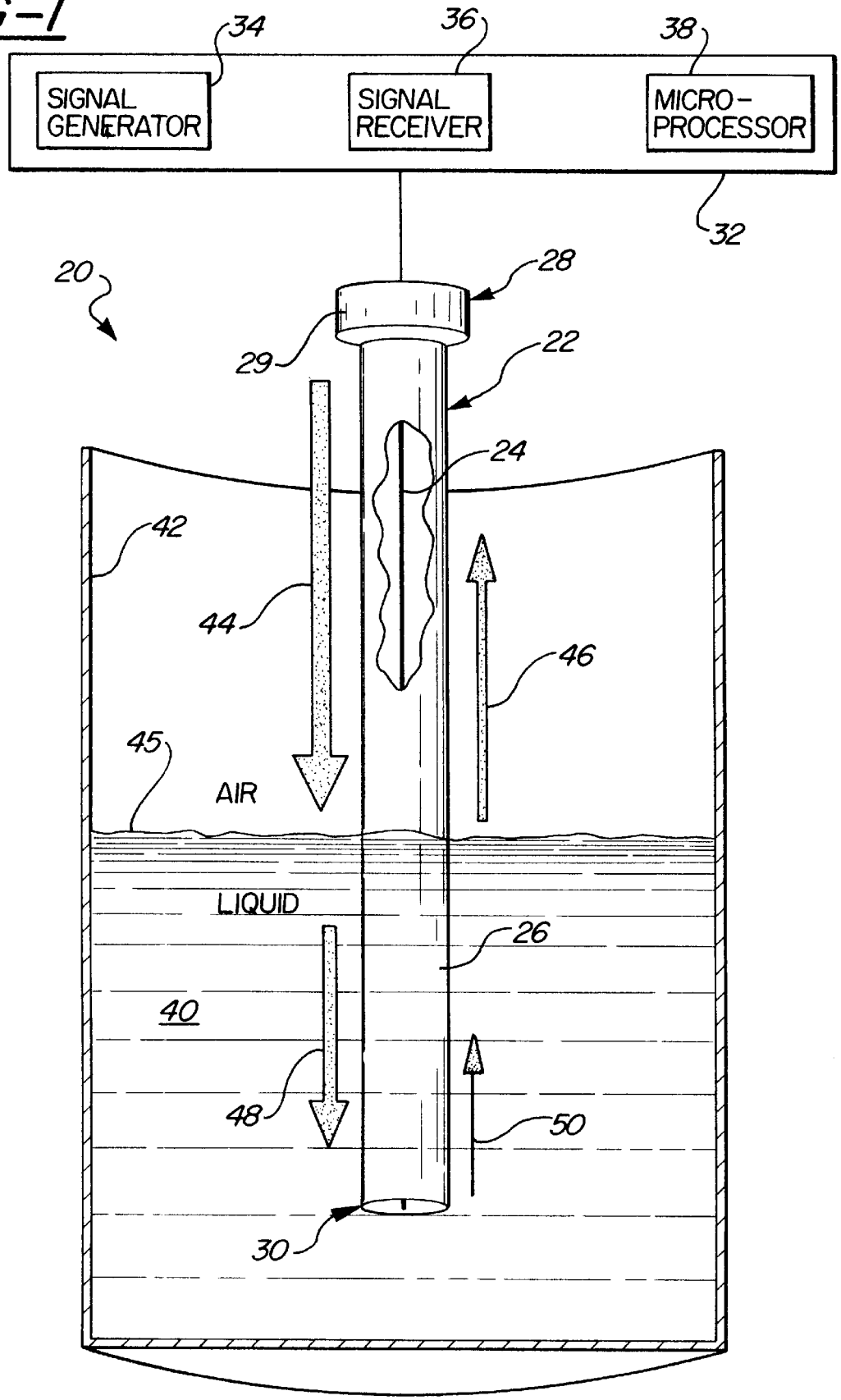
FIG. 1 is a schematic, diagrammatic illustration of a system designed according to this invention.

FIG. 1 illustrates a device 20 that is useful for measuring a level of fluid and the dielectric constant or permittivity of the fluid. A probe 22 preferably is a coaxial transmission line having an inner conductive member 24 and an outer conductive member 26. A coaxial arrangement as illustrated is not necessary to realize this invention, other transmission line arrangements can be used. The probe 22 has a first end 28, which includes a disk-like cap or mounting flange member 29 and a second end 30. Electronics 32 are coupled to the probe and include a signal generator 34, a signal receiver 36 and a microprocessor 38. The schematic illustration of the electronics 32 is intended to be by way of example only. The signal generator and receiver, for example, can be realized through a single device or appropriate software to program an appropriate microprocessor. In one embodiment, the disk-like member 29 is an electronic enclosure that houses the electronic components 34, 36 and 38.

The second end 30 of the probe 22 preferably is immersed within a fluid 40 that is maintained within a container 42. An example fluid 40 could be fuel and the container would be a fuel tank. In such an embodiment, the probe can advantageously be the fuel pick up tube.

The signal generator 34 generates a signal 44 that is propagated along the probe 22 from the first end 28 toward the second end 30. When the signal 44 encounters an interface 45 between the fluid and air, a portion of the signal is reflected as illustrated at 46. Reflection occurs because there is a different impedance between the air and the fluid. A portion of the signal continues down the probe as illustrated at 48. When the signal reaches the second end 30 the signal is reflected as illustrated at 50. The reflection occurring at the second end 30 results because the second end represents a very high impedance at the end of the probe.

The interface reflection signal can be readily distinguished from the reflection from the end of the probe because the two reflections will typically have opposite directions. The fluid 40 has a permittivity that is greater than that of air (i.e., 1.0). Therefore, the fluid 40 has a lower impedance than air. If the fluid 40 is homogenous than any positive-going reflection is from the air/fluid interface 45. A negative-going reflection is caused by the second end 30 of the probe 22. This is the usual result because the direction of the reflection is dependent on the impedance at the reflection point. The impedance at the end 30 of the probe is much higher than the impedance of the probe in the fluid 40.

This invention includes determining the dielectric constant or permittivity of the fluid 40 based upon the timing of the interface reflection signal 46 and the reflection signal 50. The timing of the reflected signals which is realized through known time domain reflectometry techniques, is used for determining permittivity based upon the following analysis.

The velocity of propagation of a signal in a medium is given by the following equation:

$$V = c/(U_r * E_r)^{1/2} \qquad \text{(equation 1)}$$

where $U_r$ is the relative permeability of the medium;
$E_r$ is the relative permittivity; and
c is the speed of light.
Velocity is also described by the following equation:

$$v = d/t \qquad \text{(equation 2)}$$

where d is distance and t is time.

It is known that air has a dielectric constant of 1. All substances and fluids, other than air, have a dielectric constant greater than 1. Further, it is known that the relative permeability (i.e. $U_r$) of non-ferrous substances is equal to 1. For purposes of this specification, it is assumed that all liquids can be classified as non-ferrous.

Since equation 1 and equation 2 both describe velocity and given the facts stated in the preceding paragraph, the relationship between the distance of travel and permittivity is described by the following equation:

$$d = t * c/(E^r)^{1/2} \qquad \text{(equation 3)}$$

Figure 2A:
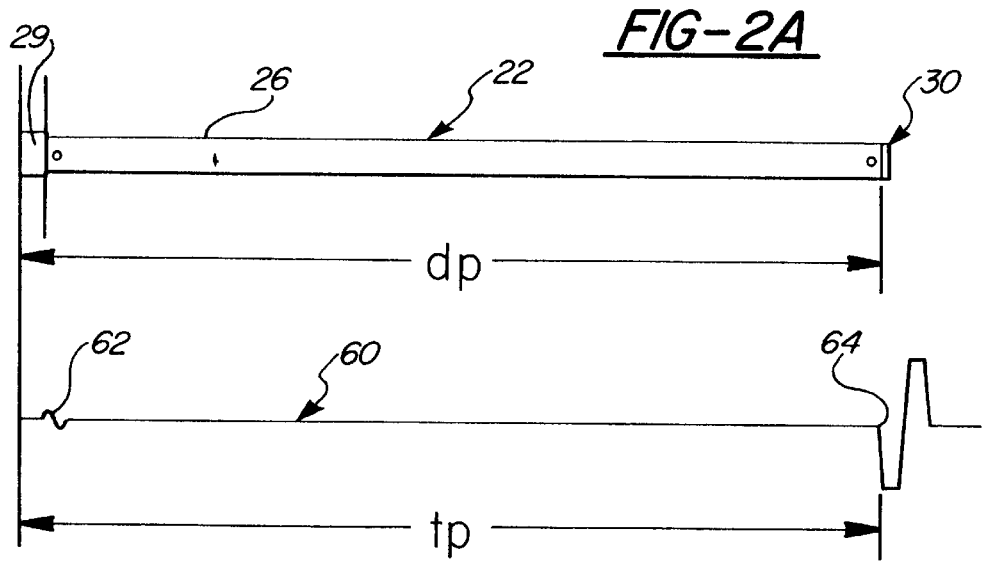
FIG. 2A is a diagrammatic illustration of a resulting wave form from a signal being propagated along a probe designed according to this invention.

FIG. 2A illustrates the probe 22 and a corresponding signal when the probe 22 is surrounded only by air. The dimension dp indicates the length of the probe 22 along which the signal travels. The curve 60 is a graphic illustration of the signal behavior including a minor impulse reflection 62 that occurs at the interface between the disk-like member 29 and the coaxial portion of the probe 22. A reflection pulse 64 occurs when the signal reaches the second end 30 of the probe 22. The time between the beginning of the signal on the probe and the time that the signal reaches the second end 30, is described as tp.

Figure 2B:
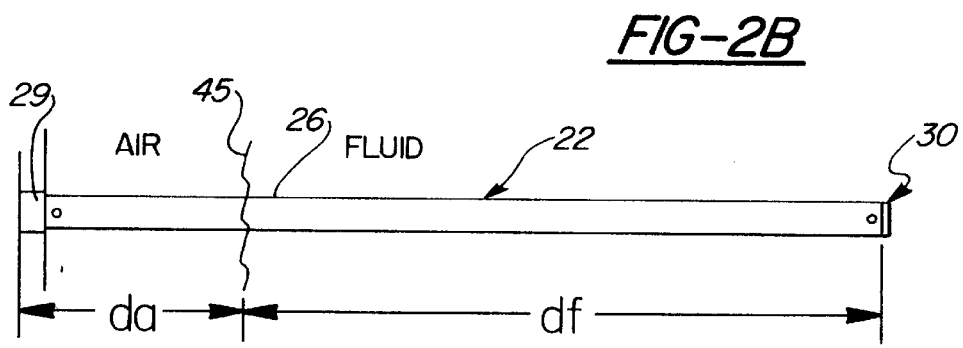
FIG. 2B diagrammatically illustrates a dimensional relationship used in the method of this invention.
Figure 2C:
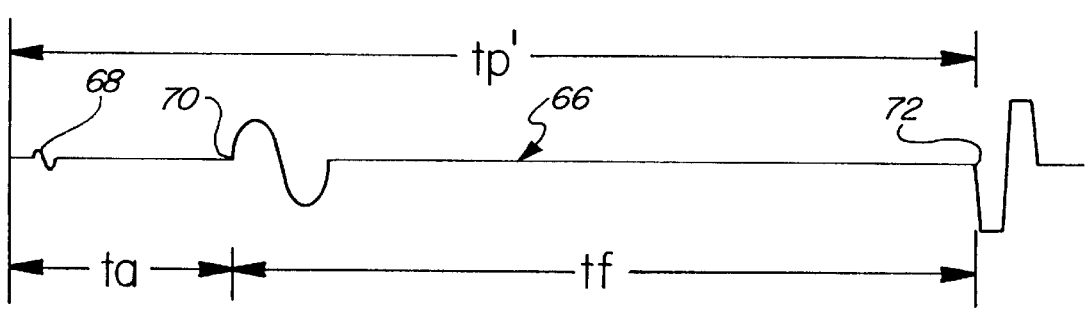
FIG. 2C diagrammatically illustrates signal behavior relative to the embodiment of FIG. 2B.

FIG. 2B illustrates the probe 22 in an environment such as that illustrated in FIG. 1. The distance between the first end of the probe 28 and the air/fluid interface 45 is described by the dimension da. The distance from the air/fluid interface 45 to the second end 30 of the probe is described as df. FIG. 2C is a timing diagram of the signal characteristic along the probe 22 as illustrated in FIG. 2B. Curve 66 includes an initial small reflection 68 like that at 62 in FIG. 2A. A first reflection pulse 70 represents the reflection of the signal 44 that occurs when the signal encounters the air/fluid interface 45. Reflection pulse 72 indicates that point at which the signal reflects from the second end 30 of the probe 22. As can be appreciated from the drawing, the total time of travel tp' is greater than the time tp illustrated in FIG. 2A. This occurs because the fluid has a higher dielectric constant than air and that reduces the velocity of propagation of the signal along the portion of the probe 22 that is immersed in the fluid.

The length of the probe is fixed. Therefore, the following equation is true:

$$dp = da + df \qquad \text{(equation 4)}$$

where the variables are those indicated in FIGS. 2A and 2B. Substituting equation 3 into equation 4 results in:

$$tp * C/(Ea)^{1/2} = (ta * C/(Ea)^{1/2}) + ((tp' - ta) * C/(E_f)^{1/2}) \qquad \text{(equation 5)}$$

where $E_a$ is the permittivity of air; and
$E_f$ is the permittivity of the fluid.
Since the permittivity of air is equal to 1, equation 5 simplifies to the following:

$$E_f = ((tp' - ta)/(tp - ta))^2 \qquad \text{(equation 6)}$$

Therefore, a relationship between the permittivity or dielectric constant $E_f$ and the time it takes the signal 44 to travel along the length of the probe 22 is established.

Figure 3:
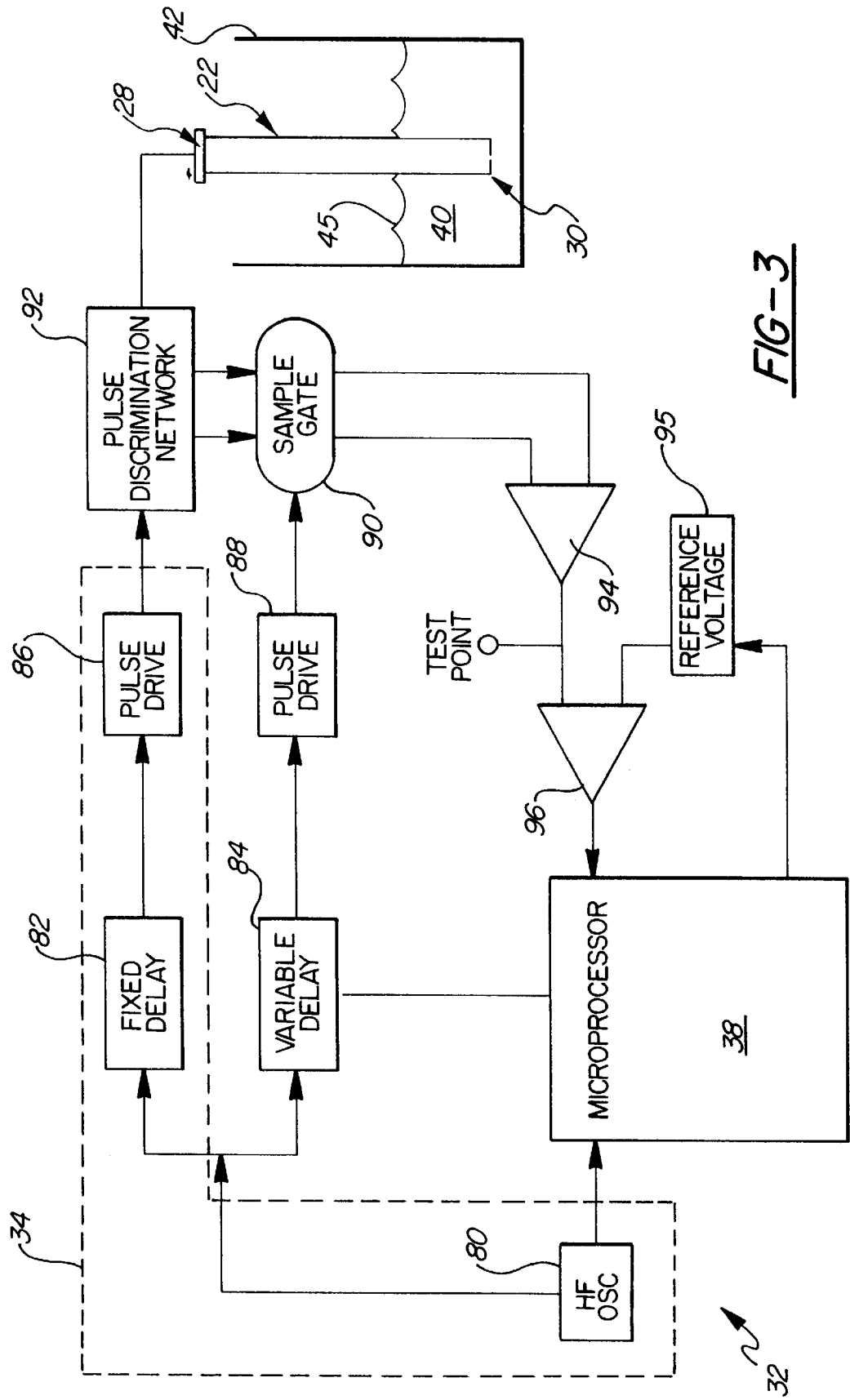
FIG. 3 schematically illustrates a presently preferred embodiment of electronics designed according to this invention.

The microprocessor 38 preferably is programmed to determine the permittivity of the fluid based upon equation 6. FIG. 3 schematically illustrates, in more detail, electronics for implementing the determination of permittivity according to this invention.

An oscillator 80 provides a clock input to microprocessor 38 and a pulse repetition rate signal that drives the signal generator 34. Delay circuits 82 and 84 provide time delays that allow equivalent time sampling techniques to be used. As known in the art, equivalent time sampling includes utilizing a single sample point during each periodic repetition of the wave form that is to be sampled. Equivalent time sampling is used, for example, in high-speed digitizing and sampling systems. Equivalent time sampling is most preferred because the number of samples taken and the sample interval determine the period of the sample wave form. Accordingly, the wave form can be down-converted in time as much as desired for a particular application. Equivalent time sampling is generally known in the art and therefore need not be further described.

Pulse drive circuits 86 and 88 are coupled to the delay circuits 82 and 84, respectively. The pulse drive circuit causes the signal 44 to be propagated along the probe 22. Pulse drive circuit 88 causes a sample gate 90 to take periodic samples of a reference transmitted signal and a combination of a propagated and reflected signal from the probe 22.

The signal 44 preferably is a micropower impulse radar signal that has a rapid rise and fall time to ensure a wide frequency spectrum. This type of signal is known in the art and those skilled in the art will be able to realize appropriate circuitry to generate such a signal by choosing from commercially available components. The preferred embodiment of this invention includes a pulse generation circuit designed according to the teachings of U.S. Pat. No. 5,609,059, which was developed at the Lawrence Livermore Laboratory.

The pulse discrimination circuitry 92 includes the signal receiver 36. As the impulse signal travels along the probe 22, reflected pulses travel back up the probe to the pulse discrimination circuitry 92. The pulse discrimination circuitry 92 preferably is a "directional sample R." The transmitted or propagated and smaller reflected pulses preferably are merged together and simultaneous samples are taken of a reference transmit signal and the merged combination of a transmitted and reflected signal. Those two signals are preferably differentially amplified in an amplifier 94 leaving only the reflected signal inputted to the level comparator 96. Microprocessor 38 controls the detect level of a comparator 96 by controlling reference voltage 95 to the comparator 96. Control of the comparator by the microprocessor allows the detection of positive going and negative going pulses. The comparator could be replaced by an analog-to-digital converter for a more detailed conversion of the signal.

The microprocessor 38 preferably includes a timer module that determines the timing of the reflections of the signal when it encounters the fluid/air interface and the second end 30 of the probe 22. Further, a permittivity module preferably is included that does the actual determination of the dielectric constant of the fluid. The timer module and permittivity module can be realized in a variety of forms. Given this specification, those skilled in the art can choose from among commercially available microprocessors or circuit components, design dedicated circuitry or develop software to realize the means for determining the dielectric constant of the fluid according to this invention.

This invention provides significant advantages compared to prior systems. The dielectric constant of the fluid is determined simply by measuring the timing of the reflection pulses. The reflection pulses can be timed with a simple timer input on low-cost, commercially available microprocessors with little or no additional circuitry, which provides the advantage of a low-cost system. Moreover, a circuit or microprocessor can be utilized that is virtually unaffected by temperature changes or long-term drift, which are problems with prior systems.

A further advantage of this invention is that constant timing errors that can occur within the system cancel out. Because all measurements are made with the same probe 22, the same timer or counter within the microprocessor 38, and the same clock source 80, any timing delay variation is present in all measurements provided that all measurements are taken within a few milliseconds of each other. Adding a constant time delay (td) to equation 6 yields:

$$E_f=((td+tp'-td+ta)/(td+tp-td+ta))^2 \quad \text{(equation 7)}$$

which simplifies as:

$$E_f=(td/td)*((tp'-ta)/(tp-ta))^2 \quad \text{(equation 8)}$$

Since td/td is equal to 1, equation 8 is equal to equation 6 and the time delay (td) has cancelled out. This cancelling effect applies to long-term or short-term drift of a clock source; any temperature drift of the clock source; a phase delay change that may be introduced in the probe or connectors caused by temperature, stretching, replacement or continued use; delay changes in the micropower impulse radar circuitry caused by temperature; and individual phase delay variations between different devices introduced by component or manufacturing variations.

Additionally, errors from phase jitter of the clock source can be removed by averaging several measurements.

Accordingly, a reliable, inexpensive and accurate method and device for determining the dielectric constant of a fluid is realized through this invention.

The preceding description is exemplary rather than limiting in nature. Variations and modifications will become apparent to those skilled in the art that do not necessarily depart from the spirit and purview of this invention. The legal scope of protection given to this invention can only be determined by studying the following claims, where the reference numerals are not be considered limiting in any way.

I claim:

1. A device (20) for determining the dielectric constant of a fluid (40), comprising:

a probe (22) having a conductive tube that is adapted to be placed at least partially into the fluid, said probe having a first end (28) and a second end (30);

a generator (34) that is coupled to said probe and generates a signal that is propagated along said probe from said first probe end toward said second probe end;

a signal receiver (36) that receives a reflection signal that is a reflection of said propagated signal from said second end of said probe; and characterized by determining means (38) for determining a time that it takes said propagated signal to travel between said first probe end and said second probe end based upon said reflection signal and for determining the dielectric constant of the fluid using said determined time.

2. The device of claim 1, wherein said determining means comprises a microprocessor (38).

3. The device of claim 2, wherein said microprocessor (38) has a first module that determines said time and a second module that is coupled with said first module and determines the dielectric constant.

4. The device of claim 3, wherein one of said modules comprises software.

5. The device of claim 3, wherein one of said modules comprises circuitry.

6. The device of claim 1, wherein a fluid/air interface (45) exists between said first and second probe ends, said signal receiver (36) receives an interface signal that is a reflection of said propagated signal from the fluid/air interface and wherein said determining means (38) further determines an interface time that it takes said propagated signal to travel between said first probe end (28) and the fluid/air interface based upon said interface signal.

7. The device of claim 6, wherein said determining means (38) determines a first time that it takes said propagated signal to travel between said first probe end (28) and said second probe end (30) based upon said reflection signal when said probe is not placed in the fluid (40) and a second time that it takes said propagated signal to travel between said first probe end (28) and said second probe end (30) based upon said reflection signal when said probe is placed in the fluid (40) and wherein said determining means determines the dielectric constant by determining a first difference between said interface time and said second time, determining a second difference between said first time and said interface time, determining a quotient by dividing said first difference by said second difference and squaring said quotient to thereby determine the dielectric constant.

8. The device of claim 6, wherein said interface signal has a first direction and said reflection signal has a second direction that is opposite from said first direction.

9. The device of claim 1, wherein said probe (22) comprises a second conductive member disposed coaxially within said conductive tube.

10. A method of determining the dielectric constant of a fluid (40), comprising the steps of:

(A) inserting a probe (22) at least partially into the fluid;

(B) generating a signal;

(C) propagating the signal along the probe;

(D) determining a travel time between the beginning of step (C) and a reflection time when the signal reflects from an end (30) on the probe;

(E) determining an interface time between the beginning of step (C) and a time when the signal reflects from an interface (45) between the fluid (40) and another medium adjacent the fluid; and (F) determining the dielectric constant of the fluid using the travel time from step (D) and the interface time from step (E).

11. The method of claim 10, wherein step (F) includes using a calibration time to thereby determine the dielectric constant.

12. The method of claim 11, wherein step (E) is performed by determining a first difference between the travel time and the interface time, determining a second difference between the calibration time and the interface time, determining a quotient by dividing the first difference by the second difference and squaring the quotient to thereby determine the dielectric constant.

13. The method of claim 12, further including the step of predetermining the calibration time by placing the probe (22) in a medium having a known dielectric constant value, performing steps (B), (C) and (D) with the probe in the medium and determining the calibration time to be the travel time with the probe in the medium.

14. The method of claim 10, wherein step (A) is performed by inserting a portion of the probe (22) into the liquid (40) such that a remaining portion of the probe is surrounded by air and a fluid/air interface (45) exists at some point along a length of the probe and wherein the method further comprises the step of determining an interface time between the beginning of step (C) and an interface reflection time when the signal reflects from the fluid/air interface.

15. The method of claim 14, wherein step (E) is performed using the following equation:

$$E_f = ((tp'-ta)/(tp-ta))^2$$

where tp'=the travel time from step (D);

ta=the interface time; and tp=a calibration factor.

16. The method of claim 15, further comprising predetermining the calibration factor by placing the probe (22) in air, performing steps (B), (C) and (D) with the probe in air and determining the calibration factor to be the travel time with the probe in air.

17. The method of claim 14, further comprising the steps of discriminating between the interface reflection time and the travel time by determining a first direction associated with the reflection of the signal from the fluid/air interface (45) and a second direction associated with the reflection of the signal from the end of the probe (22).

18. A device (20) for determining the dielectric constant of a fluid (40), comprising:

a probe (22) that is adapted to be placed at least partially into the fluid, said probe having a first end (28) and a second end (30) that is placed into the fluid;

a generator (34) that is coupled to said probe and generates a signal that propagated along said probe from said first probe end toward said second probe end;

a signal receiver (36) that receives an interface signal, which is a reflection of said propagated signal from an interface between the fluid and an adjacent medium and a reflection signal, which is a reflection of said propagated signal from said second end of said probe;

a computer (38) having a timer module that determines a first time that it takes said propagated signal to travel between said first probe end and the interface based upon the interface signal and a second time that it takes said propagated signal to travel between said first probe end and said second probe end based upon said reflection signal and a dielectric constant module that utilizes said first and second time determined by said timer module and determines the dielectric constant of the fluid.

19. The device (20) of claim 18, wherein one of said modules comprises software.

20. The device (20) of claim 18, wherein said probe (22) is partially immersed in the fluid (40) and the interface comprises a fluid/air interface (45) between said probe ends, and wherein said first time is an interface time when said signal reflects from said interface, and said dielectric constant module determines the dielectric constant based upon the following relationship:

$$E_f = ((tp'-ta)/(tp-ta))^2$$

where tp' equals the second time it takes the signal to travel between said first and second probe ends;

ta equals said interface time, and tp equals a calibration factor.

* * * * *